US009675696B2

(12) United States Patent
Chamness (10) Patent No.: US 9,675,696 B2
(45) Date of Patent: *Jun. 13, 2017

(54) METHOD AND USE FOR INCREASING EFFICACY OF ANTI-ADHESIVE COMPOSITIONS IN CONTROLLING INFLAMMATION AND PAIN

(75) Inventor: Kathy L. Chamness, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1557 days.

This patent is subject to a terminal disclaimer.

(21) Appl. No.: 11/598,397

(22) Filed: Nov. 14, 2006

(65) Prior Publication Data

US 2008/0112921 A1 May 15, 2008

(51) Int. Cl.
*A61K 8/72* (2006.01)
*A61K 45/06* (2006.01)
*A61K 31/77* (2006.01)
*A61K 33/06* (2006.01)

(52) U.S. Cl.
CPC .............. *A61K 45/06* (2013.01); *A61K 31/77* (2013.01); *A61K 33/06* (2013.01)

(58) Field of Classification Search
USPC ..................................................... 424/70.11
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,605,687 A | 2/1997 | Lee et al. | |
| 5,686,488 A * | 11/1997 | Gamache et al. | 514/549 |
| 6,037,331 A | 3/2000 | Shalaby et al. | |
| 6,630,167 B2 | 10/2003 | Zhang | |
| 6,656,459 B2 | 12/2003 | Kabanov et al. | |
| 6,869,938 B1 | 3/2005 | Schwartz et al. | |
| 7,582,680 B1 | 9/2009 | Shi et al. | |
| 7,837,987 B2 | 11/2010 | Shi et al. | |
| 8,153,112 B2 * | 4/2012 | Drapeau | A61K 31/74 424/422 |
| 2002/0136719 A1 * | 9/2002 | Shenoy et al. | 424/130.1 |
| 2003/0083231 A1 * | 5/2003 | Ahlem | A61K 31/56 514/26 |
| 2003/0118545 A1 | 6/2003 | Shi et al. | |
| 2004/0037893 A1 * | 2/2004 | Hansen et al. | 424/682 |
| 2004/0214790 A1 | 10/2004 | Borgens | |
| 2004/0258757 A1 * | 12/2004 | Bosch et al. | 424/489 |
| 2005/0069520 A1 | 3/2005 | Shi et al. | |
| 2005/0074495 A1 | 4/2005 | Schwartz et al. | |
| 2006/0067976 A1 * | 3/2006 | Ferraro et al. | 424/426 |
| 2007/0258938 A1 | 11/2007 | Roy et al. | |

FOREIGN PATENT DOCUMENTS

| | | |
|---|---|---|
| GB | 1250304 A | 10/1971 |
| GB | 1286351 A | 8/1972 |
| WO | WO01/28544 A | 4/2001 |
| WO | 02092107 | 11/2002 |

OTHER PUBLICATIONS

Borgens et al. "Immediate Recovery from spinal cord injury through molecular repair of nerve membranes with polyethylene glycol" FASEB J. 2000, 14, pp. 27-35.*
Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.
Borgens R B and Bohnert D., "Rapid recovery from spinal cord injury after subcutaneously administered polyetheylene glycol," Journal of Neuroscience Research (2001); vol. 66, pp. 1179-1186.
Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.
The International Search Report and the Written Opinion of the International Searching Authority in PCT/US2007/067580.
Apan, A. et al., Postoperative magnesium sulphate infusion reduces analgesic requirements in spinal anaesthesia, European Journal of Anaesthesiology, May 2004;21:766-769.
Bhatia, A. et al., Effect of Intraoperative Magnesium Infusion on Perioperative Analgesia in Open Cholecystectomy, Journal of Clinical Anesthesia, Jun. 2004;16(4):262-265.
Bigal, ME et al., Intravenous magnesium sulphate in the acute treatment of migraine without aura and migrain with aura, Cephalalgia, Jan. 2002;22(5):345-353.
Bolcal, C. et al., Comparison of Magnesium Sulfate With Opioid and NSAIDs on Postoperative Pain Management After Coronary Artery Bypass Surgery, Journal of Cardiothoracic and Vascular Anesthesia, Dec. 2005;19(6):714-718.
Brill, S. et al., Efficacy of intravenous magnesium in neuropathic pain, British Journal of Anaesthesia, May 2002;89(5):711-714.
Cete, Y. et al., A randomized prospective placebo-controlled study of intravenous magnesium sulphate vs. metoclopramide in the management of acute migraine attacks in the Emergency Department, Cephalalgia, May 2004;25(3):199-204.
Corbo, J. et al., Randomized Clinial Trial of Intravenous Magnesium Sulfate as an Adjunctive Medication for Emergency Department Treatment of Migraine Headache, Dec. 2001;38(6):621-627.
Crosby, V. et al., The Safety and Efficacy of a Single Dose (500 mg or 1g) of Intravenous Magnesium Sulfate in Neuropathic Pain Poorly Responsive to Strong Opioid Analgesics in Patients with Cancer, Journal of Pain and Symptom Management, Jan. 2000;19(1):35-39.
Felsby, S. et al., NMDA receptor blockade in chronic neuropathic pain: a comparison of ketamine and magnesium chloride, Pain, Feb. 1995;64(2):283-291.
Hoane, M.R. et al., The behavioral effects of magnesium therapy on recovery of function following bilateral anterior medial cortex lesions in the rat, Brain Research Bulletin, Apr. 2003;60(1-2):105-114.
Izumi, Y. et al., Reduction of Infarct Volume By Magnesium After Middle Cerebral Artery Occlusion in Rats, Journal of Cerebral Blood Flow and Metabolism, Nov. 1991;11(6):1025-1030.
McCartney, C.J. et al., A Qualitative Systematic Review of the Role of N-Methyl-D-Aspartate Receptor Antagonists in Preventive Analgesia, Anesth Analg. May 2004;98(5):1385-1400.
McIntosh, T.K. et al., Magnesium protects against neurological deficit after brain injury, Brain Research, Mar. 1989;482(2):252-260.
Moulin, D.E. et al., Systemic Drug Treatment for Chronic Musculoskeletal Pain, The Clinical Journal of Pain, Dec. 2001;17(4 Suppl):S86-S93.

(Continued)

Primary Examiner — James Rogers (57) ABSTRACT

A method and kits thereof for increasing the efficiency of anti-adhesive compositions by parenterally administering a composition comprising an effective amount of at least one pharmaceutically-acceptable anti-adhesive non-ionic polymer to a site of injury, controlling inflammation at the site of injury, and reducing pain.

16 Claims, 5 Drawing Sheets

(56) References Cited

OTHER PUBLICATIONS

Russell, I.J. et al., Treatment of Fibromyalgia Syndrome with Super Malic®: A Randomized, Double Blind, Placebo Controlled, Crossover Pilot Study, Journal of Rheumatology, May 1995;22(5):953-958.
Tramer, M.R. et al., Magnesium bier's block for treatment of Chronic limb pain: a randomised, double-blind, cross-over study, Pain, Sep. 2002;99(1-2):235-241.
Turner, R.J. et al., Magnesium Gluconate Offers No More Protection than Magnesium Sulphate Following Diffuse Traumatic Brain Injury in Rats, Jounal of the American College of Nutrition, Oct. 2004;23(5):541S-544S.
Vink R. et al., Pharmacological and physiological effect of magnesium on experimental traumatic brain injury, Magnesium Research, Sep. 1990;3(3):163-169.
Muir et al., Magnesium for acute stroke (Intravenous Magnesium Efficacy in Stroke trial): randomised controlled trial, The Lancet, Feb. 2004;363(9407):439-445.
Saver, J.L. et al., Prehospital Neuroprotective Therapy for Acute Stroke: Results of the Field Administration of Stroke Therapy-Magnesium (FAST-MAG) Pilot Trial, Stroke, Mar. 2004;35(5):106-108.
Bittner, G.D. et al., Reconnection of severed nerve axons with polyethylene glycol, Brain Research, 1986; 367(1-2):351-355.
Shapiro, S. et al., Oscillating field stimulation for complete spinal cord injury in humans: a Phase 1 trial, J Neurosurg Spine, Jan. 2005; 2(1):3-10.
Resende, M.A. et al., Local transcutaneous electrical stimulation (TENS) effects in experimental inflammatory edema and pain, European Journal of Pharmacology, Sep. 2004; 504(1):217-222.
Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).
Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).
Kwon, et al. "Translational Research in Spinal Cord Injury: A Survey of Opinion from the SCI Community," Journal of Neurotrauma, 27, pp. 21-33 (Jan. 2010).
McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).
Journal of Spinal Cord Medicine, 34(6), 620-621 (2011).

* cited by examiner

Polyoxyethylene sorbitan monoester

Polyoxyethylene sorbitan triester

FIG. 4

Poly(lactide)

Poly(glycolide)

Poly(lactide-co-glycolide)

Polycaprolactone

Poly(lactide-co-caprolactone)

FIG. 5

METHOD AND USE FOR INCREASING EFFICACY OF ANTI-ADHESIVE COMPOSITIONS IN CONTROLLING INFLAMMATION AND PAIN

FIELD OF THE INVENTION

The present invention relates to methods of increasing efficacy of anti-adhesive compositions by parental administration of compositions containing anti-adhesive polymers and magnesium salts. More particularly local inflammation at a site of injury is controlled and pain is reduced in post-surgery injuries.

BACKGROUND OF THE INVENTION

Pain in general is associated with a myriad of medical conditions and affects millions of Americans. As reported by the American Pain Foundation, over 50 million Americans suffer from chronic pain including 20% of individuals aged 60 and over who are affected by joint disorders such as arthritis. Furthermore, nearly 25 million Americans experience acute pain due to injuries or surgical procedures each year. In addition to its economical burden, pain has a tremendous effect on the quality of life of affected individuals and is one of the most common causes of disability.

Cell-adhesion interactions are crucial for a broad range of physiological processes, including inflammation, immunity, and hemostasis. Cell adhesion is a process by which cells associate with each other, migrate towards a specific target or localize within the extra-cellular matrix. Among fundamental mechanisms underlying numerous biological phenomena, cell adhesion is responsible for the adhesion of hematopoietic cells to endothelial cells and the subsequent migration of those hematopoietic cells out of blood vessels and to the site of inflammatory injury. As such, cell adhesion plays a role in numerous pathologies such as, for example, inflammation and immune reactions in mammals. In failed back syndrome, cell adhesion complicates revision surgeries and an effective method to decrease adhesive occurrence and tenacity would be beneficial. Particularly a method that involves a formula that reduces the pain tenacity is beneficial.

Investigations into the molecular basis for cell adhesion have revealed that various cell-surface macromolecules— collectively known as cell adhesion molecules or receptors—mediate cell-cell and cell-matrix interactions. For example, proteins of the superfamily called "integrins" are key mediators in adhesive interactions between hematopoietic cells and their micro environment. M. E. Hemler, "VLA Proteins in the Integrin Family: Structures, Functions, and Their Role on Leukocytes", Ann. Rev. Immunol., 8, p. 365 (1990).

Alpha 4 beta1 integrin, also known as very late antigen of activation-4 ("VLA-4") or CD49d/CD29, is a leukocyte cell surface receptor that participates in a wide variety of both cell-cell and cell-matrix adhesive interactions. M. E. Hemler, Ann. Rev. Immunol., 8, p. 365 (1990). It serves as a receptor for the cytokine-inducible endothelial cell surface protein, vascular cell adhesion molecule-1 ("VCAM-1"), as well as to the extracellular matrix protein fibronectin ("FN"). Ruegg, et al., J. Cell Biol., 177, p. 179 (1991); Wayner, et al., J. Cell Biol., 105, p. 1873 (1987); Kramer et al., J. Biol. Chem., 264, p. 4684 (1989); Gehlsen, et al., Science, 24, p. 1228 (1988). Anti-VLA4 monoclonal antibodies have been shown to inhibit VLA-4-dependent adhesive interactions both in vitro and in vivo. Ferguson, et al., Proc. Natl. Acad. Sci., 88, p. 8072 (1991); Ferguson, et al., J. Immunol., 150, p. 1172 (1993). Results of in vivo experiments suggest that the inhibition of VLA-4-dependent cell adhesion should prevent, inhibit or alter several inflammatory and autoimmune pathologies. R. L. Lobb, et al., J. Clin. Invest., 94, pp. 1722-28 (1994). See also Kabanov, et al., U.S. Pat. No. 6,656,459, for example, entitled Compositions of Non-Ionic Block Copolymers to Treat Autoimmune and Inflammatory Diseases, And To Reduce Graft/Implantation, and Methods of Use Thereof, issued Dec. 3, 2003.

Cell adhesion in tissues were minimized by use Polyethylene Glycol (PEG) to forming steric barrier between tissues. See WO9910022 issued Mar. 4, 1999 and WO9903481 issued Jan. 28, 1999. Crosslinking PEG and polyacids to form gels in inhibiting cell adhesion are disclosed in U.S. Pat. No. 6,869,938 to Schwartz et. al., Compositions of Polyacids and Polyethers and Methods for Their Use In Reducing Adhesions, issued Mar. 22, 2005. Crosslinked hyaluronic acid gels to inhibit cell adhesion is described in U.S. Pat. No. 6,630,167 to Zhang et. al., Hyaluronic Acid Anti-Adhesion Barrier, issued Oct. 7, 2003.

Hyaluronic acid gel compositions containing non-steroidal anti inflammatory drugs (NSAIDs) and excess of organic divalent metal salts including magnesium were used for prevention of adhesion and inflammation. Such compositions were found to have increased residence times in biological environments and in vivo animal studies reduced adhesion formation. See U.S. Pat. No. 6,037,331 to Shalaby et. al., Compositions For Prevention Of Inflammation And Adhesion Formation Uses Thereof, issued Mar. 1, 2000.

Magnesium has been found to act as a blocker of nerve cell. N-methyl-D-aspartate receptors (NMDAR) which activates neural sensitization. Thus neuropathic pain and its resultant inflammation was reduced. See M. Jones, "Chronic Neuropathic Pain: Pharmacological In The New Millennium", International J. Pharmaceutical Compounding, January-February 2000.

Given the above, methods useful for increasing the efficiency of inhibition, alteration, or prevention of cell adhesion and cell adhesion-mediated pathologies are needed. For example, prevention and/or treatment of inflammatory and autoimmune diseases, and reduction of pain is needed in particularly post-surgery.

SUMMARY OF THE INVENTION

The present invention addresses this and other problems associated with the prior art by providing a method for increasing the efficacy of anti-adhesive compositions comprising: parenterally administering a composition comprising an effective amount of at least one pharmaceutically-acceptable anti-adhesive non-ionic polymer and at least one magnesium salt to a site of injury; controlling inflammation at the site of injury: and reducing the pain.

While not being bound by any theory, the applicants believe that the at least one magnesium salt forms a complex with the oxygen groups of the anti-adhesive non-ionic polymer, for example alkylene oxide groups of the anti-adhesive non-ionic polymer in biological environments. Such complexes provide for the synergistic effects of magnesium salts and non-ionic polymers and increases the efficiency of anti-adhesion mechanisms.

The invention is further directed to methods wherein the composition comprises an effective amount of at least one pharmaceutically-acceptable anti-adhesive non-ionic polymer which is selected from the group consisting of polyethylene glycol(PEG), polyoxyethylene-polyoxypropylene copolymer, polyethylene oxide, polyoxyethylene alkyl ether, polyoxyethylene stearate, polyoxyethylene sorbitan fatty acid ester, macrogol 15 hydroxystearate, aliphatic polyesters, and hyaluronan.

In addition, the present invention is directed to methods wherein the composition is administered proximal in time after creation of the injury, particularly when the injury is a surgery, for example, selected from orthopedic surgery, neurosurgery, insertion of a medical device, organ transplant surgery, and vascular surgery.

In a further aspect the present invention comprises an effective amount of at least one agent selected from the group consisting of an analgesic agent, an anti-inflammatory agent and an immunosuppressant.

The present invention is further directed to a kit for control of inflammation at a site of injury and pain comprised of a composition comprising an effective amount of at least one pharmaceutically-acceptable anti-adhesive non-ionic polymer, at least one magnesium salt, and instructions associated therewith which indicate parenteral administration of the composition to the site for control of inflammation and pain. The discovery of a synergistic effect between PEG, an anti-adhesive non-ionic polymer, and magnesium salt is highly significant as it can lead to the development of therapeutic formulations with improved efficacy for the treatment of neuronal trauma, inflammatory and painful conditions.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Definitions

To aid in the understanding of the invention, the following non-limiting definitions are provided:

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "subject" includes a living or cultured system upon which the methods and/or kits of the current invention is used. The term includes, without limitation, humans.

The term "practitioner" means a person who practices methods, kits, and compositions of the instant invention on the subject. The term includes, without limitations, doctors, other medical personnel, and researchers.

The terms "neuropathic pain" and "neural origin pain" refer to pain initiated or caused by a pathological condition of the nervous system, including, without limitation, pathology following chronic or acute insults.

The hallmarks of neuropathic pain are chronic allodynia and hyperalgesia. Accordingly, the term "allodynia" refers to pain resulting from a stimulus that ordinarily does not elicit a painful response.

The term "hyperalgesia" refers to an increased sensitivity to a normally painful stimulus. Primary hyperalgesia affects the immediate area of the injury.

The term "secondary hyperalgesia" or "referred pain" is normally utilized in cases when sensitization has extended to a broader area surrounding the injury.

The term "neuronal injury" refers to an insult to an element of the central or peripheral nervous systems. Neuronal injuries can be derived from a physical (including mechanical, electrical or thermal), ischemic, hemorrhagic, chemical, biological or biochemical insult. Examples of neuronal injuries include, without limitations, ischemic and hemorrhagic stroke, spinal cord, brain, cranial nerve and peripheral nerve injuries.

The term "bioactive agent" refers to molecules and physical stimuli.

The term "biological environment" refers to the environment where anti-adhesive effects takes place. Examples include, without limitation, site of injury and site of inflammation.

The term "complex" refers to the interaction between magnesium metal and the electrons of the oxygen groups of the non-ionic polymer. Without limitation such oxygen groups comprises of alkylene oxide groups for example polyoxyethylene groups and polyoxypropylene groups.

Compositions of this invention may be used alone or in combination with other therapeutic or prophylactic agents to inhibit, alter, prevent or suppress cell adhesion.

All references to chemical compounds, including without limitation, anti-adhesive non-ionic polymers, bio-active agents, include all forms of these chemical compounds (i.e., salts, esters, hydrates, ethanolates, etc.), wherein said forms possess at least partial activities of the respective chemical compounds.

Pain and Inflammation

There are two basic forms of physical pain: acute and chronic. Acute pain, for the most part, results from disease, inflammation, or injury to tissues. It is mediated by activation of sensory fibers also known as nociceptive neurons. Nociceptive pain normally disappears after healing, for example in cases of post-traumatic or post-operative pain. Unfortunately, in some individuals, pathological changes occur that increase the sensitivity of the sensory neurons. In those cases, symptomatic pain can become chronic and persists for months or even years after the initial insult.

Neuronal injuries are complex clinical conditions aggravated by a variety of precipitating causes that influence the severity of injury and ultimately influence the course and extent of recovery. A primary insult to a component of the central and/or peripheral nervous system could be of mechanical, chemical, biological or electrical nature. Following the primary insult, a cascade of biochemical and physiological events takes place that often leads to pathobiological changes that are considered largely responsible for the development of irreversible damages. This autodestructive cascade is known as secondary injury and because it develops over time after the traumatic event it opens a window of opportunity for pharmacological interventions. Various chronic conditions linked to persistent on-going tissue damage due, for example, to inflammatory reactions or autoimmune diseases, may also lead to secondary injury of neuronal components and symptomatic pain.

Inflammation is the body's normal protective response to conditions that include a tissue necrosis component. Tissue necrosis can be derived from a physical (including mechanical, electrical or thermal), chemical, biological or biochemical insult. Clinical conditions with an inflammatory component include traumatic tissue injury, surgery, degenerative diseases such as arthritis and other joint diseases as well as irritation, hypersensitivity, and auto-immune reactions.

During this natural "defense" process, local increases in blood flow and capillary permeability lead to accumulation of fluid, proteins and immune cells in the inflamed area. Some of these cells can release chemical mediators of inflammation including histamine, cytokines, bradykinin and prostaglandins that can attract more immune cells at the site of inflammation and/or increase the sensitivity of pain fibers within the affected area. As the body mounts this protective response, the symptoms of inflammation develop. These symptoms include, without limitation, pain, swelling and increased warmth and redness of the skin. The inflammatory response has to be tightly regulated otherwise it may lead to tissue necrosis and development of chronic pain.

Embodiment injectable formulations and related methods are described herein that interfere with the adhesion of immune cells to damaged tissues, grafts or organ transplants as well as surrounding tissue. Embodiment methods particularly reduce the invasion of treated tissues by activated immune cells and prevent and/or reduce the severity of an anti-inflammatory cascades that lead to further tissue damage and serious chronic conditions. Embodiment methods of prophylactic treatment, for example, are provided which follow tissue damage (accidental injury or post-surgery, for example) to reduce inflammation and prevent the development of associated chronic conditions such as pain and hypersensitivity. Methods described herein may also be used to increase the success rate of any implant, graft or transplant procedure. Methods and compositions of the present invention prevent the attachment of micro-organisms (e.g., bacteria, fungus) and allergens to mucous membranes that can trigger an immune reaction.

Embodiment methods of the present invention control inflammation, pain, and hypersensitivity, for example, at a site of recent tissue injury, as at a surgical site. In another embodiment processes described herein prevent inflammation in tissues particularly if administered after tissue damage but before an inflammatory reaction is initiated. Administration of compositions described herein to injured tissue, including blood vessels, in a mammal significantly reduces the entry of immune cells which promote inflammation.

Methods of the present invention comprise, for example, administering at least one pharmaceutically acceptable anti-adhesive polymer and at least one magnesium salt by means of injection to a site of recently injured tissue. Compositions described herein may also be administered to a site of ongoing inflammation.

Embodiment of anti-adhesive non-ionic polymers and compositions thereof described herein may be in the form of liquid, gel, or solid (implant). Injectable formulations are preferred. Compositions described herein may remain as liquid or gel depot(s), for example, in vivo. Methods of the present invention, for example, comprise injecting a polymeric depot to prevent the attachment of immune cells within the area surrounding a site of administration.

Another embodiment also relates to the treatment of cytokine-mediated diseases, including TNF alpha-induced and/or IL-1, IL-1 beta, IL-6, and/or IL-8 induced diseases and/or chemokine-mediated diseases. "Chemokines" are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GRO-alpha, GRO-beta, GRO-gamma, ENA-78, GCP-2, IP-10, MIG and PF4. CC chemokines include RANTES, MIP-1.alpha., MIP-2.beta., monocyte chemotactic protein-1 (MCP-1), MCP-2, MCP-3 and eotaxin. Example chemokines includes but are not limited to IP-10, MCP-1, RANTES, and SDF-1. Related mediators include but are not limited to lipopolysaccharide-biding protein, TLR4, CD-14, GM-CSF, and G-CSF.

An embodiment of the present invention also relates to pharmaceutical formulations capable of inhibiting TNF alpha-induced vascular cell adhesion molecule-1 (VCAM-1) expression and the resulting leukocyte-endothelial cell adhesion for the inhibition and prevention of inflammation.

Formulations described herein may also be used in co-therapies, partially or completely, in place of other conventional anti-inflammatories, such as together with steroids, cyclooxygenase-2 inhibitors, NSAIDs, DMARDS, antibiotics, immunosuppressive agents, 5-lipoxygenase inhibitors, $LTB_4$ antagonists and $LTA_4$ hydrolase inhibitors and anti-cell adhesion molecules, such as anti E-selectin.

Methods

Methods of controlling inflammation at a site of injury are provided which comprise parenterally administering an effective amount of a composition which comprises an effective amount of anti-adhesive non-ionic polymer and at least one magnesium salt, for example, to the site. Methods of the present invention are preferred wherein the anti-adhesive polymer and the at least one magnesium salt is administered proximal in time after creation of the injury. The term "proximal in time" as used herein refers to a time that is within six (6) hours of the injury, e.g., between about five (5) seconds after the injury to about six (6) hours after the injury. Preferably compositions described herein are administered in methods of the present invention between about one (1) minute after the injury to about one (1) hour after the injury. Methods of the present invention are preferred wherein a surgery is a creation of the injury. The term "surgery" as used herein refers to operations including but not limited to orthopedic surgery, neurosurgery, insertion of a medical device, organ transplant surgery, and vascular surgery.

Anti-Adhesive Non-Ionic Polymers

Anti-adhesive non-ionic polymers for employment in methods as well as compositions of the present invention include polymers such as PEG. Agents that have hydroscopic properties and/or mobile molecular arm(s), for example, are preferred agents. Pharmaceutically-acceptable non-ionic polymers are suitable. Preferred anti-adhesive non-ionic polymers for employment in methods and compositions of the present invention include, but are not limited to PEG (polyethyleneglycol), polyoxyethylene-polyoxypropylene co-polymer, polyethylene oxide, polyoxyethylene alkyl ether, polyoxyethylene stearate, polyoxyethylene sorbitan fatty acid ester, macrogol 15 hydroxystearate, aliphatic polyesters, and hyaluronan. The preferred characteristics of the anti-adhesive non-ionic polymers for employment in methods and compositions of the present invention are that they are able to be applied via syringe and that the formulation is adherent to wet tissue. Anti-adhesive non-ionic polymers for employment in methods and compositions of the present invention can either be viscous or set up in situ. In a preferred embodiment of the anti-adhesive non-ionic polymers for employment in methods and compositions of the present invention, the pH is neutral and the composition is aqueous. Although the dosage will depend on the type of surgery employed, which the skilled worker in the field will understand, about 10 mL of the compositions of the instant invention are employed to coat tissue surfaces after surgery. One of skill in the art will recognize however, that multiple doses could be used for a large surgical procedure with multiple surgical sites.

PEG

Preferred compositions comprise at least one PEG. Polyethylene glycols (PEGs) are widely used in a variety of pharmaceutical formulations including parenteral, including biodegradable polymeric matrices used in controlled-release systems. Pharmaceutical Excipients, Eds. Raymond C Rowe, Paul J Sheskey and Siân C Owen, London: Pharmaceutical Press (2006).

Figure 1:
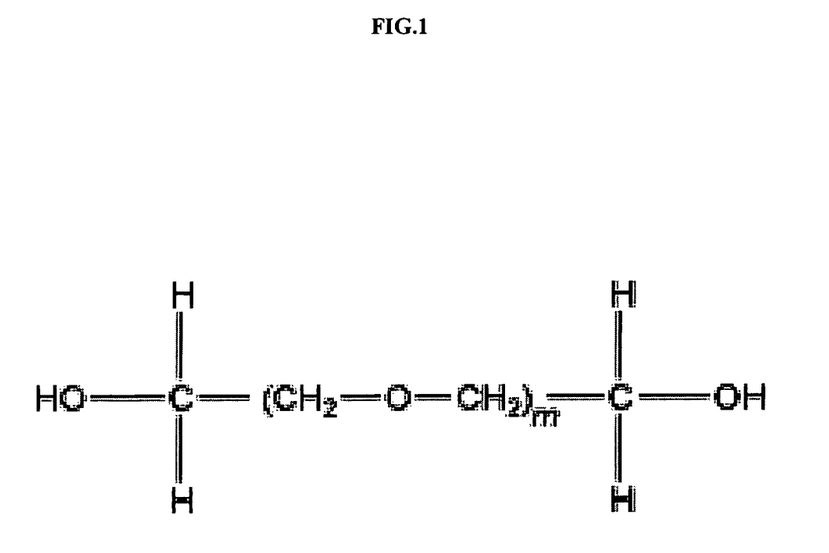
FIG. 1 displays the general structure of Polyethylene Glycol (PEG) (α-Hydro-ω-hydroxypoly(oxy-1,2-ethanediyl)) $HOCH_2(CH_2OCH_2)_m CH_2OH$ where m represents the average number of oxyethylene groups.

PEG has a general formula (α-Hydro-ω-hydroxypoly (oxy-1,2-ethanediyl) as shown in FIG. 1. A representative example of PEG is $HOCH_2(CH_2OCH_2)_mCH_2OH$ where m represents the average number of oxyethylene groups. Alternatively, the general formula $H(OCH_2CH_2)_nOH$ may be used to represent PEG, where n is a number m in the previous formula+1. See, e.g., Ademovic Z, et al., *The Method of Surface Pegylation Influences Leukocyte Adhesion and Activation*, J. Mater. Sci. Mater. Med., 17(3):203 (2006); Serra, L., et al., *Design of Poly(ethylene glycol)-Tethered Copolymers as Novel Mucoadhesive Drug Delivery Systems*, 63(1):11 (2006). PEG hydrogel carriers are mucoadhesive and can be used for protein delivery. Peppas, N. A., et al., *Poly(ethylene glycol)-Containing Hydrogels in Drug Delivery*, J. Control Release, 62(1-2):81 (1999).

PEG grades 200-600 are liquids; grades 1000 and above are solids at ambient temperatures. Liquid grades (PEG 200-600) occur as clear, colorless or slightly yellow-colored, viscous liquids. In concentrations up to approximately 30% v/v, PEG 300 and PEG 400, for example, may be used for parenteral dosages. Liquid PEG's are very hygroscopic, although hygroscopicity decreases with increasing molecular weight. All grades of PEG are soluble in water and miscible in all proportions with other PEGS. The chemical reactivity of PEGS is mainly confined to the two terminal hydroxyl groups, which can be either esterified or etherified.

Mixtures of PEGS can be used. Liquid grades are generally employed with the consistency being adjusted by the addition of solid grades of PEG, for example. The rate of release of water-soluble medications, for example, decreases with the increasing molecular weight of the PEG.

Aqueous PEG solutions can be used. PEGs for use in compositions of the present invention include but are not limited to PEG 200, PEG 300, PEG 400, PEG 600, and PEG 800. CARBOWAX®, CARBOWAX SENTRY®, LIPOXOL®, LUTROL E®, PLURIOL E®.

Suitable PEGS, for example, are selected from the group consisting of PEG 200, PEG 300, PEG 400, PEG 600, and PEG 800.

Polyoxyethylene-Polyoxypropylene Co-Polymers

Figure 2:
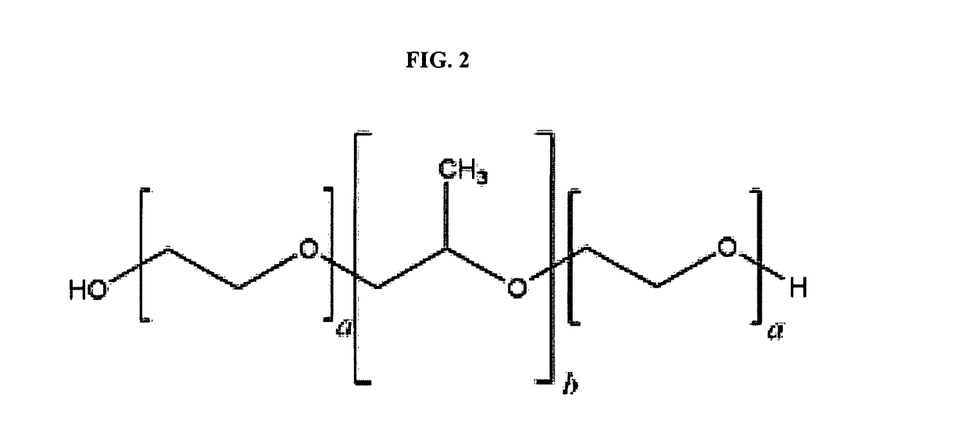
FIG. 2 shows the general structure of Polyoxyethylene-polyoxypropylene co-polymer (α-Hydro-ω-hydroxypoly(oxyethylene)poly(oxypropylene) poly(oxyethylene) block copolymer). $(C_2H_4O)_a(C_3H_6O)_b(C_2H_4O)_a H$. The polyoxyethylene segment is hydrophilic while the polyoxypropylene segment is hydrophobic.

Further preferred compositions of the present invention comprise an effective amount of at least one Polyoxyethylene-polyoxypropylene co-polymer (α-Hydro-ω-hydroxy-poly(oxyethylene)poly(oxypropylene) poly(oxyethylene) block copolymer) (CAS 9003-11-6) (e.g., PLURONIC®, LUTROL®). In the USA the trade name PLURONIC® is used by BASF Corp. for pharmaceutical-grade poloxamers, while in Europe the trade name LUTROL® is used by BASF Corp. for the pharmaceutical-grade material. The poloxamer polyols are a series of closely related block copolymers of ethylene oxide and propylene oxide conforming to the general formula $HO(C_2H_4O)_a(C_3H_6O)_b(C_2H_4O)_aH$, as shown in FIG. 2.

Poloxamers are nonionic polyoxyethylene-polyoxypropylene copolymers. The polyoxyethylene segment is hydrophilic while the polyoxypropylene segment is hydrophobic. All poloxamers are chemically similar in composition, differing only in the relative amounts of propylene and ethylene oxides added during manufacture. Their physical and surface-active properties vary over a wide range and a number of different types are commercially available.

Poloxamer 188 has also been used as an emulsifying agent for fluorocarbons used as artificial blood substitutes and in the preparation of solid-dispersion systems. Poloxamers have been employed in drug-delivery systems. See, e.g., Anderson B C, et al., *Understanding Drug Release from Poly(ethylene oxide)-B-(propylene oxide)-B-Poly(ethlene oxide)Gels*, J Control Release, 70:157 (2001); Alakhov V, et al. Pluronic Block Copolymers and Pluronic Poly(acrylic acid) Microgels in Oral Delivery of Megestrol Acetate, J Pharm Pharmacol, 56:1233 (2004). The disclosure of Kabanov, et al., U.S. Pat. No. 6,656,459, entitled Compositions of Non-Ionic Block Copolymers to Treat Autoimmune and Inflammatory Diseases, and to Reduce Graft/Implantation, and Methods of Use Thereof, issued Dec. 3, 2003, is herein incorporated by reference.

Poloxamers generally occur as white, waxy, free-flowing prilled granules, or as cast solids. They are practically odorless and tasteless. At room temperature, poloxamer 124 occurs as a colorless liquid.

TABLE I

Typical Poloxamer Grades

| Poloxamer | Physical form | a | B | Average molecular weight |
|---|---|---|---|---|
| 124 | Liquid | 12 | 20 | 2090–2360 |
| 188 | Solid | 80 | 27 | 7680–9510 |
| 237 | Solid | 64 | 37 | 6840–8830 |
| 338 | Solid | 14 | 44 | 12700–17400 |
| 407 | Solid | 10 | 56 | 9840–14600 |

Poloxamer 188 (Highly purified poloxamer 188 (trade name FLOCOR®)), for example, alters the way cells and molecules interact with water. Extensive preclinical studies suggest that iv. administration of poloxamer 188 improves microvascular blood flow in ischaemic tissues by inhibiting adhesive interactions, lowering blood viscosity and reducing friction along the vessel wall, for example. Expert Opin Investig Drugs, 7(7):1193 (1998).

Although the USPNF 23 contains specifications for five poloxamer grades, many more different poloxamers are commercially available that vary in their molecular weight and the proportion of oxyethylene present in the polymer. A series of poloxamers with greatly varying physical properties are thus available.

Suitable polyoxyethylene-polyoxypropylene Co-polymers, for example, are selected from the group consisting of Poloxamer 124, Poloxamer 188, Poloxamer 237, Poloxamer 338, and Poloxamer 407.

Polyethylene Oxide

Embodiment compositions of the present invention comprise an effective amount of at least one Polyethylene Oxide. Polyethylene oxide [CAS 25322-68-3] (polyoxyethylene) is a mucoadhesive compound. The USPNF 23 describes polyethylene oxide as a nonionic homopolymer of ethylene oxide, represented by the formula $(CH_2CH_2O)_n$, where n represents the average number of oxyethylene groups. The higher molecular weight grades provide delayed drug release via the hydrophilic matrix approach. The relationship between swelling capacity and molecular weight is a good guide when selecting products for use in immediate- or sustained-release matrix formulations. Polyethylene oxide can be radiation crosslinked in solution to produce a hydrogel. Polyethylene oxide has a low level of toxicity regardless of the route of administration. See, e.g., Yu D M, et al., *Viscoelastic Properties of Poly(ethylene oxide) Solution*, J Pharm Sci; 83: 1443 (1994); Dhawan S, et al., *High Molecular Weight Poly(ethylene oxide)-Based Drug Delivery Systems: Hydrogels and Hydrophilic Matrix Systems*. Pharm Technol, 29(5):72-74, 76-80 (2005).

Polyoxyethylene Alkyl Ethers

Embodiment compositions of the present invention comprise an effective amount of at least one Polyoxyethylene alkyl ether:

In the formula, (x+1) is the number of carbon atoms in the alkyl chain, typically:

12 lauryl(dodecyl); 14 myristyl(tetradecyl); 16 cetyl (hexadecyl); 18 stearyl(octadecyl)

and y is the number of ethylene oxide groups in the hydrophilic chain, typically 10-60.

The polyoxyethylene alkyl ethers tend to be mixtures of polymers of slightly varying molecular weights, and the numbers quoted are average values. In cetomacrogol 1000, for example, x is 15 or 17, and y is 20-24.

The polyoxyethylene alkyl ethers are a series of polyoxyethylene glycol ethers of n-alcohols (lauryl, oleyl, myristyl, cetyl, and stearyl alcohol). Of the large number of different materials commercially available, four types are listed in the USPNF 23, i.e., Polyoxyl 20 cetostearyl ether, Polyoxyl 10 oleyl ether, Polyoxyl lauryl ether, and Polyoxyl stearyl ether. Polyoxyethylene alkyl ethers are nontoxic. BRIJ® 97 (15-20%) (Imperial Chemical Industries, Wilmington Del.), VOLPO® N (Croda Inc., Edison, N.J.) series and CREMOPHOR® A25 (21-30%) (BASF Corp., Florham Park, N.J.) provide clear gels.

Polyoxyethylene alkyl ethers such as polidocanol are suitable for use in injectable formulations.

Polyoxyethylene Stearates

Embodiment compositions of the present invention comprise an effective amount of at least one polyoxyethylene stearate. Polyoxyethylene stearates (poly(oxy-1,2-ethanediyl) α-hydro-ω-hydroxyoctadecanoate) are non-ionic compounds, e.g., polyoxyl 40 stearate.

Structure A applies to the monostearate; where the average value of n is 6 for polyoxyl 6 stearate, 8 for polyoxyl 8 stearate, and so on.

Structure B applies to the distearate; where the average value of n is 12 for polyoxyl 12 distearate, 32 for polyoxyl 32 distearate, and so on.

In both structures, R represents the alkyl group of the parent fatty acid. With stearic acid, R is $CH_3(CH_2)_{16}$. However, it should be noted that stearic acid usually contains other fatty acids, primarily palmitic acid, and consequently a polyoxyethylene stearate may also contain varying amounts of other fatty acid derivatives such as palmitates.

Polyoxyethylene stearates are generally used as emulsifiers in oil-in-water-type creams and lotions. Their hydrophilicity or lipophilicity depends on the number of ethylene oxide units present: the larger the number, the greater the hydrophilic properties. Polyoxyl 40 stearate, for example, has been used as an emulsifying agent in intravenous infusions.

Suitable polyoxyethylene stearates are one selected from the group consisting of Polyoxyl 20 cetostearyl ether, Polyoxyl 10 oleyl ether, Polyoxyl lauryl ether, Polyoxyl stearyl ether, and polyoxyl 40 stearate.

Polyoxyethylene Sorbitan Fatty Acid Esters

Embodiment compositions of the present invention comprise an effective amount of at least one polyoxyethylene sorbitan fatty acid ester. Polyoxyethylene sorbitan fatty acid esters (polysorbates) are a series of partial fatty acid esters of sorbitol and its anhydrides copolymerized with approximately 20, 5, or 4 moles of ethylene oxide for each mole of sorbitol and its anhydrides. The resulting product is therefore a mixture of molecules of varying sizes rather than a single uniform compound as shown, for example, in FIG. 3.

Figure 3:
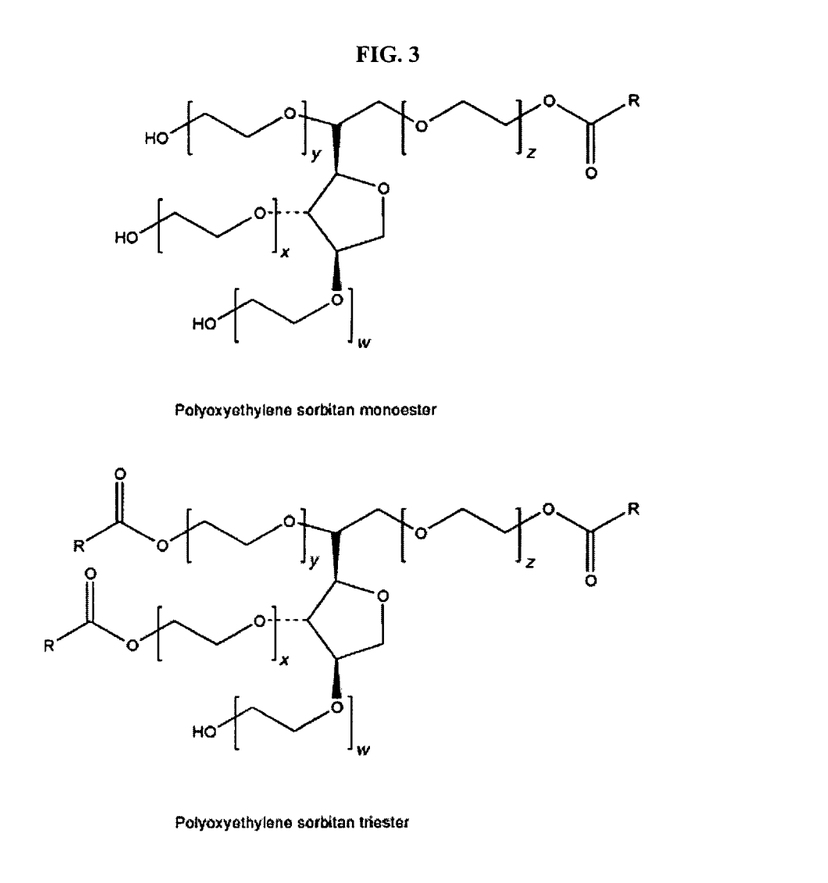
FIG. 3 illustrates the general structure of polyoxyethylene sorbitan fatty acid esters (polysorbates) are a series of partial fatty acid esters of sorbitol and its anhydrides copolymerized. w+x+y+z=20 (Polysorbates 20, 40, 60, 65, 80, and 85). R=fatty acid.

In that figure, w+x+y+z=20, 40, 60, 65, 80 or 85 (Polysorbates 20, 40, 60, 65, 80, and 85 respectively); and R=fatty acid Polysorbates containing 20 units of oxyethylene are hydrophilic nonionic surfactants that are used widely as emulsifying agents in the preparation of stable oil-in-water, for example, pharmaceutical emulsions. They may also be used as solubilizing agents in the formulation of parenteral suspensions. Polysorbates 20, 40, 60 and 80 are included in the FDA Inactive Ingredients Guide (IV preparations).

Suitable polyoxythylene sorbitan fatty acid esters are, for example, selected from the group consisting of Polysorbate 20, Polysorbate 40, Polysorbate 60, and Polysorbate 80.

Macrogol 15 Hydroxystearate

Embodiment compositions of the present invention comprise an effective amount of macrogol 15 hydroxystearate (polyethylene glycol-15-hydroxystearate (CAS 70142-34-6)) in concentrations up to 60%.

Aliphatic Polyesters

Figure 4:
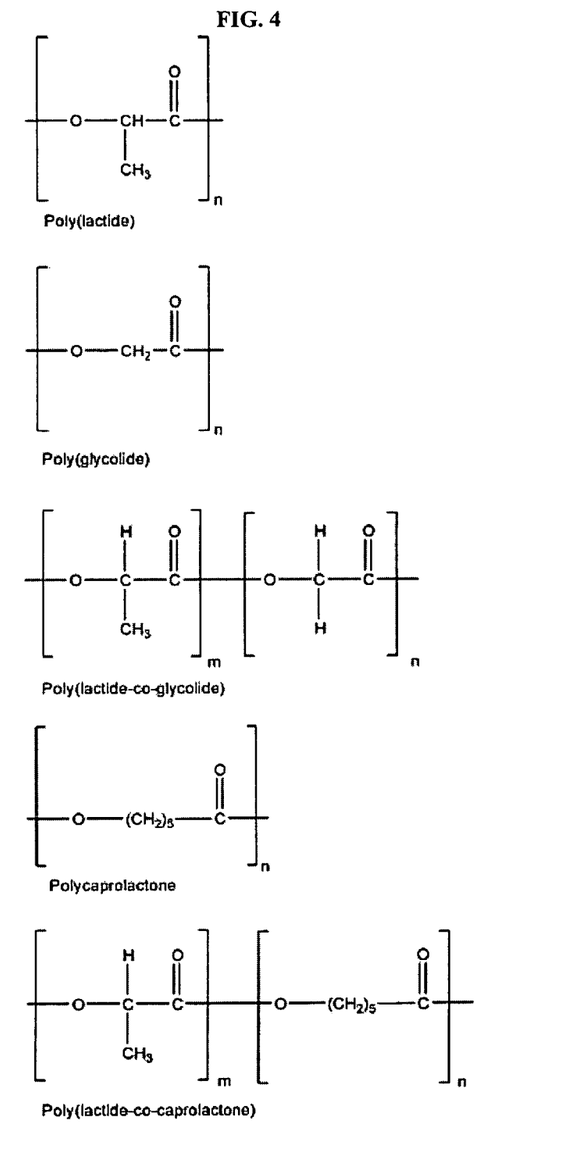
FIG. 4 displays the general structure of aliphatic polyesters, i.e., synthetic homopolymers or copolymers of lactic acid, glycolic acid, and ϵ-hydroxycaproic acid. Typically, the molecular weights of homopolymers and copolymers range from 2000 to >100000.

Embodiment compositions of the present invention comprise an effective amount of at least one aliphatic polyester. Aliphatic polyesters are synthetic homopolymers or copolymers of lactic acid, glycolic acid, and ε-hydroxycaproic acid. Typically, the molecular weights of homopolymers and copolymers range from 2000 to >100 000, representative examples of which are shown in FIG. 4.

Aliphatic polyesters are a group of synthesized, nontoxic, biodegradable polymers. In an aqueous environment, they undergo hydrolytic degradation, through cleavage of the ester linkages, into nontoxic hydroxycarboxylic acids. Aliphatic polyesters are eventually metabolized to carbon dioxide and water, via the citric acid cycle. Owing to their reputation as safe materials and their biodegradability, aliphatic polyesters are primarily used as biocompatible and biodegradable polymers for formulation of many types of implantable and injectable drug-delivery systems and liquid injectable controlled-release systems. The rate of biodegradation and drug-release characteristics from these systems formulated with the aliphatic polyesters can be controlled by changing the physicochemical properties of the polymers, such as crystallinity, hydrophobicity, monomer stereochemistry, copolymer ratio, and polymer molecular weight.

Poly(lactide), poly(glycolide), poly(lactide-co-glycolide), and polycaprolactone are used in parenteral pharmaceutical formulations and are regarded as biodegradable, biocompatible, and bioabsorbable materials. See, e.g., Kissel T, et al., *Properties of Block and Random Copolymers of Lactic Acid and Glycolic Acid*, Proc Int Symp Control Rel Bioact Mater, 20:127 (1993).

Sodium Hyaluronate

Figure 5:
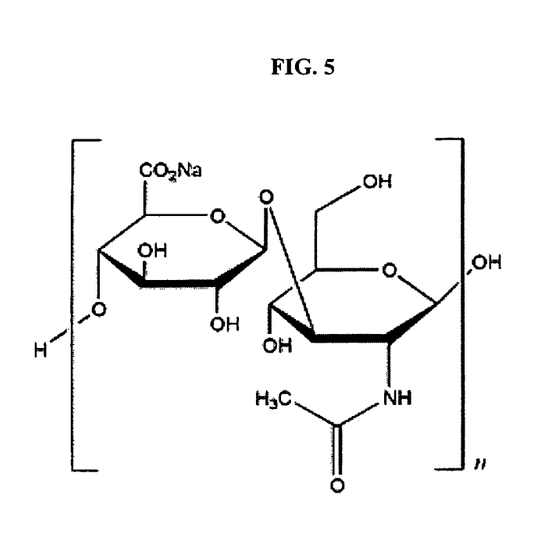
FIG. 5 shows the general structure of sodium hyaluronate $(C_{14}H_{20}NO_{11}Na)_n$.

Embodiment compositions of the present invention comprise an effective amount of sodium hyaluronate or an anti-adhesive derivative thereof. Sodium hyaluronate (CAS 9067-32-7) is a humectant or matrix for sustained release formulations. $(C_{14}H_{20}NO_{11}Na)_n$ (401.3)n, as shown, for example, in FIG. 5. Sodium hyaluronate is the predominant form of hyaluronic acid at physiological pH. The name hyaluronan is used when the polysaccharide is mentioned in general terms, and in the literature the terms hyaluronic acid and sodium hyaluronate are used interchangeably.

Hyaluronan is used therapeutically to treat osteoarthritis in the knee, and is an effective treatment for arthritic pain. Castellacci E, et al., *Antalgesic Effect and Clinical Tolerability of Hyaluronic Acid in Patients with Degenerative Diseases of Knee Cartilage*, Drugs Exp Clin Res., 30(2):67 (2004).

Crosslinked hyaluronan gels are used as drug delivery systems. Hyaluronan and crosslinked derivatives thereof provide an effective barrier against adhesions. HYALO-GLIDE® (a highly viscous hyaluronan derivative absorbable gel)

HYALOBARRIER® is obtained from pure hyaluronan through an auto-crosslinking process. J. Orthop. Res., 23(6):1377 (2005).

Magnesium Salts

The present invention comprises an anti adhesive non-ionic polymer in combination with a magnesium salt is useful for the treatment of neuronal trauma and painful conditions.

Accordingly, in one embodiment of the invention, the anti-adhesive composition comprises at least one magnesium salt. Magnesium plays an important role in a large diversity of cellular functions. For example, magnesium is required for glycolysis and oxidative phosphorylation which support energy-producing and energy-consuming reactions in cells. Protein synthesis as well as membrane structure and function are also magnesium-dependent. Levels of magnesium will affect neurotransmitter release including glutamate and acetylcholine release. It also regulates the activity of calcium transporters and opening of the non-methyl-D-aspartate (NMDA) glutamate receptors. Magnesium is known to have anti-oxidant, anti-apoptosis and to modulate lipid formation and transport. In addition to its cellular effects, magnesium can modulate physiological functions involved in regulation of blood flow and edema development.

Magnesium supplementation has been extensively studied in animals and humans for its ability to reduce acute and chronic pain. However, mixed results have been reported from clinical trials evaluating the efficacy of magnesium (alone or in combination) in reducing pain associated with various surgical procedures (Bolcal et al., 2005; Apan et al., 2004; Bathia et al., 2004; McCartney et al., 2004), headache and acute migraine attacks (Cete et al., 2005; Corbo et al., 2001; Bigal et al, 2002), peripheral neuropathies (Brill et al., 2002; Felsby et al., 1996), cancer (Crosby et al., 2000), primary fibromyalgia syndrome (Moulin, 2001; Russel et al., 1995) and chronic limb pain (Tramer and Glynn, 2002). In addition, it appears that magnesium analgesic effect may be of a short duration such as 4 hours or less (Crosby et al., 2000). Magnesium may also induce side effects such as flushing and aching that can reduce its therapeutic window (Tramer and Glynn, 2002). Magnesium supplementation therapies can be achieved by using various salts including magnesium sulfate, chloride, gluconate and magnesium-ATP leading to similar neuroprotective effects in animal models of CNS injury (McIntosh et al., 1989; Izumi et al., 1991; Hoane et al., 2003; Turner et al., 2004; reviewed in Vink and McIntosh, 1990).

In an embodiment, at least one magnesium salt comprises magnesium sulfate, magnesium chloride, magnesium gluconate, magnesium ATP, or any combination thereof. In another embodiment, at least one magnesium compound forms a complex with the oxygen groups of the anti-adhesive non-ionic polymer. Preferably, at least one magnesium compound forms a complex with the alkylene oxide group of the anti-adhesive non-ionic polymer.

Analgesic Agents, Anti-Inflammatory Agents and Immunosuppressants

Further the invention is directed to methods wherein the composition further comprises an effective amount of at least one agent selected from the group consisting of an analgesic agent, an anti-inflammatory agent and an immunosuppressant.

Analgesic Agents

Methods and compositions of the present invention are preferred wherein at least one analgesic agent is selected from the group consisting of an NSAID and a salicylate.

Nonsteroidal anti-inflammatory drugs (NSAIDs), for example, are a well-known group of unrelated organic acids that have analgesic, anti-inflammatory, and antipyretic properties. NSAIDs are inhibitors of the enzyme cyclo-oxygenase, and so directly inhibit the biosynthesis of prostaglandins and thromboxanes from arachidonic acid. There are 2 forms of cyclo-oxygenase (COX), COX-1, which is the constitutive form of the enzyme, and COX-2, which is the form induced in the presence of inflammation. Inhibition of COX-2 is therefore responsible for at least some of the analgesic, anti-inflammatory, and antipyretic properties of NSAIDs. In regular dosage NSAIDs have both a lasting analgesic and an anti-inflammatory effect which makes them particularly useful for the treatment of continuous or regular pain associated with inflammation. NSAIDs are used for the relief of mild to moderate pain, minor febrile conditions, and for acute and chronic inflammatory disorders. NSAIDs for use in compositions of the present invention include but are not limited to Aceclofenac, Acemetacin, Alminoprofen, Aminophenazone, Aminopropylone, Ampiroxicam, Amtolmetin Guacil, Azapropazone, Bendazac, Benoxaprofen, Benzydamine, Beta-aminopropionitrile, Bromfenac, Bufexamac, Bumadizone, Butibufen Sodium, Carprofen, Celecoxib, Clofexamide, Clofezone, Clonixin, Dexibuprofen (the active enantiomer of ibuprofen), Diclofenac, Dipyrone, Droxicam, Eltenac, Epirizole, Etodolac, Etofenamate, Etoricoxib, Felbinac, Fenbufen, Fenoprofen, Fentiazac, Fepradinol, Feprazone, Floctafenine, Flufenamic Acid, Flunixin, Flunoxaprofen, Flurbiprofen, Furprofen, Glafenine, Glucametacin, Ibuprofen, Ibuproxam, Indometacin, Isonixin, Kebuzone, Ketoprofen, Ketorolac, Lonazolac, Lornoxicam, Loxoprofen, Meclofenamate, Mefenamic Acid, Meloxicam, Mofebutazone, Mofezolac, Morniflumate, Nabumetone, Naproxen, Nifenazone, Niflumic Acid, Nimesulide, Oxaprozin, Oxyphenbutazone, Parecoxib, Phenazone, Phenylbutazone, Piketoprofen, Piroxicam, Pranoprofen, Proglumetacin, Propyphenazone, Proquazone, Ramifenazone, Rofecoxib, Sulindac, Suprofen, Suxibuzone, Tenoxicam, Tetridamine, Tiaprofenic Acid, Tiaramide, Tolfenamic Acid, Tolmetin, Valdecoxib, Vedaprofen, Zaltoprofen.

Aspirin and other salicylates have analgesic, anti-inflammatory, and antipyretic properties. Like other NSAIDs they are inhibitors of the enzyme cyclo-oxygenase; however, aspirin (though not the non-acetylated salicylates) irreversibly acetylates the enzyme whereas other NSAIDs compete with arachidonic acid for the active site. Salicylates are used for the relief of mild to moderate pain, minor febrile conditions, and for acute and chronic inflammatory disorders.

Salicylates for use in compositions of the present invention include but are not limited to Aspirin, Aloxiprin, Aluminium Aspirin, Ammonium Salicylate, Amyl Salicylate, Bornyl Salicylate, Carbasalate Calcium, Choline Magnesium Trisalicylate, Choline Salicylate, Diethylamine Salicylate, Diflunisal, Ethenzamide, Ethyl Salicylate, Fosfosal, Glycol Salicylate, Imidazole Salicylate, Lithium Salicylate, Lysine Aspirin, Magnesium Salicylate, Methyl Butetisalicylate, Methyl Salicylate, Morpholine Salicylate, Picolamine Salicylate, Salamidacetic Acid, Salicylamide, Salix, Salol, Salsalate, Sodium Salicylate, Sodium Thiosalicylate, Thurfyl Salicylate, Trolamine Salicylate.

Anti-Inflammatory Agents

Methods and compositions of the present invention are further preferred wherein at least one anti-inflammatory agent is selected from the group consisting of a corticosteroid and an anti-inflammatory biopharmaceutical. Corticosteroids commonly employed in local corticosteroid injections are preferred, i.e., Dexamethasone, Dexamethasone phosphate, Hydrocortisone acetate, Methylprednisolone acetate, Prednisolone acetate, and Triamcinolone acetonide.

Corticosteroids

By "corticosteroid" is meant any naturally occurring or synthetic steroid hormone which can be derived from cholesterol and is characterized by a hydrogenated cyclopentanoperhydrophenanthrene ring system. Exemplary corticosteroids include for use in compositions of the present invention include, for example, Alclometasone Dipropionate, Aldosterone, Amcinonide, Beclometasone Dipropionate, Bendacort, Betamethasone, Budesonide, Ciclesonide, Ciprocinonide, Clobetasol Propionate, Clobetasone Butyrate, Clocortolone Pivalate, Cloprednol, Cortisone Acetate, Cortivazol, Deflazacort, Deprodone, Desonide, Desoximetasone, Desoxycortone Acetate, Dexamethasone, Dichlorisone Acetate, Diflorasone Diacetate, Diflucortolone, Difluprednate, Fluclorolone Acetonide, Fludrocortisone Acetate, Fludroxycortide, Flumetasone Pivalate, Flunisolide, Fluocinolone Acetonide, Fluocinonide, Fluocortin Butyl, Fluocortolone, Fluorometholone, Fluprednidene Acetate, Fluprednisolone, Fluticasone Propionate, Formocortal, Halcinonide, Halometasone, Hydrocortamate Hydrochloride, Hydrocortisone, Isoflupredone Acetate, Loteprednol Etabonate, Mazipredone, Medrysone, Meprednisone, Methylprednisolone, Mometasone Furoate, Paramethasone Acetate, Prednicarbate, Prednisolone, Prednisone, Prednylidene, Procinonide, Resocortol Butyrate, Rimexolone, Suprarenal Cortex, Tixocortol Pivalate Triamcinolone, and Ulobetasol Propionate.

Anti-Inflammatory Biopharmaceuticals

Methods and compositions of the present invention are further preferred wherein at least one anti-inflammatory agent is selected from the group consisting of Abatacept (ORENCIA®); Adalimumab (HUMIRA®); Anakinra (KINERET®); Etanercept (ENBREL®); Infliximab (REMICADE®); and Leflunomide (ARAVA®).

Abatacept (ORENCIA®). Abatacept is given by intravenous infusion over a period of 30 minutes in the following doses: 500 mg for patients weighing less than 60 kg, 750 mg for those weighing 60 to 100 kg, and 1 g for those over 100 kg. The dose is repeated at 2 and 4 weeks, then every 4 weeks thereafter. See, e.g., Genovese, M C, et al. *Abatacept For Tumor Necrosis Factor Alpha Inhibition*, N Engl J Med, 353:1114 (2005). Adalimumab (HUMIRA®). Adalimumab is a monoclonal tumor necrosis factor antibody used alone or with methotrexate, for example. It is given by subcutaneous injection in a dose of 40 mg every other week; some patients not receiving methotrexate may benefit from increasing the dose to 40 mg every week. See, e.g., van de Putte L B, et al., *Efficacy and safety of Adalimumab as Monotherapy*, Ann Rheum Dis; 63:508 (2004); Keystone E C, et al., *Concomitant Methotrexate Therapy: A Randomized, Placebo-Controlled, 52-Week Trial, Arthritis Rheum,* 50:1400 (2004).

Anakinra (KINERET®). Anakinra is a recombinant receptor antagonist of interleukin-1, an inflammatory mediator. See, e.g., Schiff M H, Drugs, 64: 2493 (2004). The usual dose is 100 mg once daily by subcutaneous injection. The dose should be given at about the same time each day.

Etanercept (ENBREL®). Etanercept is a recombinant version of soluble human tumor necrosis factor (TNF) receptor that binds specifically to tumor necrosis factor and blocks its interaction with endogenous cell-surface TNF receptors. See, e.g., Klareskog L, et al., Lancet, 363:675 (2004). Infliximab (REMICADE®). Infliximab is a chimeric monoclonal antibody to tumor necrosis factor alpha (TNF), a pro-inflammatory mediator. Infliximab is given in a dose of 3 mg/kg, repeated at 2 and 6 weeks, then every 8 weeks thereafter, in combination with methotrexate. In the USA, the dose may be increased up to 10 mg/kg or repeated as often as every 4 weeks in those with an incomplete response.

Leflunomide (ARAVA®). Leflunomide has immunosuppressant and antiproliferative properties. See, e.g., Miceli-Richard C, et al., Expert Opin Pharmacother; 4:987 (2003).

Immunosuppressants

Methods and compositions of the present invention are further preferred wherein at least one immunosuppressant is selected from the group consisting of Abetimus Sodium, Antilymphocyte Immunoglobulins, Azathioprine, Basiliximab, Brequinar Sodium, Ciclosporin, Daclizumab, Everolimus, Gavilimomab, Gusperimus Hydrochloride, Inolimomab, Mizoribine, Muromonab-CD3, Mycophenolate, Repertaxin 1-lysine, Sirolimus, Tacrolimus.

Kits

A kit is provided herein for control of inflammation at a site of injury comprised of a composition comprising an effective amount of at least one pharmaceutically-acceptable anti-adhesive non-ionic polymer, at least one magnesium salt and instructions associated therewith which indicate parenteral administration of the composition to the site for increased efficiency of anti-adhesive properties. Embodiment kits of the present invention are preferred wherein the composition further comprises an effective amount of at least one agent selected from the group consisting of an analgesic agent, an anti-inflammatory agent and an immunosuppressant.

Specific embodiments according to the methods of the present invention will now be described in the following non-limiting examples. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of increasing the efficacy of anti-adhesive compositions, the method comprising: after creation of a neuronal injury and prior to inflammation at the site of the injury parenterally administering an injectable liquid composition comprising an effective amount of a pharmaceutically-acceptable anti-adhesive non-ionic polymer mixture, and a magnesium salt to the site of injury; controlling inflammation at the site of injury; and reducing pain, wherein the pharmaceutically-acceptable anti-adhesive non-ionic polymer mixture consists of PEG (polyethylene glycol) at a concentration of 30% volume per volume of the composition and sodium hyaluronate, and the magnesium salt consists of magnesium chloride which forms a complex with the oxygen groups of PEG; wherein the injectable liquid composition is not a gel.

2. The method according to claim 1 wherein the anti-adhesive non-ionic polymer is administered between one minute and one hour after creation of the injury.

3. The method according to claim 1 wherein a surgery is a creation of the injury.

4. The method according to claim 3 wherein the surgery is selected from the group consisting of orthopedic surgery, neurosurgery, and insertion of a medical device.

5. The method according to claim 1 wherein the composition further comprises an effective amount of at least one agent selected from the group consisting of analgesic agents, anti-inflammatory agents and immunosuppressants.

6. The method according to claim 5 wherein at least one analgesic agent is selected from the group consisting of an NSAID and a salicylate.

7. The method according to claim 5 wherein at least one anti-inflammatory agent is selected from the group consisting of a corticosteroid and an anti-inflammatory biopharmaceutical.

8. The method according to claim 5 wherein at least one immunosuppressant is selected from the group consisting of Abetimus Sodium, Antilymphocyte Immunoglobulins, Azathioprine, Basiliximab, Brequinar Sodium, Cyclosporin, Daclizumab, Everolimus, Gavilimomab, Gusperimus Hydrochloride, Inolimomab, Mizoribine, Muromonab-CD3, Mycophenolate, Repertaxin 1-lysine, Sirolimus, or Tacrolimus.

9. A method of increasing the efficacy of anti-adhesive compositions, the method comprising: parenterally administering an injectable liquid composition comprising an effective amount of a pharmaceutically-acceptable anti-adhesive non-ionic polymer mixture and a magnesium salt or the site of a neuronal injury; controlling inflammation at the site of injury; and reducing pain, wherein the anti-adhesive non-ionic polymer mixture consists of PEG (polyethylene glycol) at a concentration of 30% volume per volume of the composition and sodium hyaluronate and the magnesium salt consists of magnesium chloride which forms a complex with the oxygen groups of PEG; wherein the injectable liquid composition is not a gel.

10. The method of claim 9, wherein the neuronal injury comprises a spinal cord injury.

11. The method of claim 9, wherein the neuronal injury comprises a brain injury.

12. The method of claim 9, wherein the neuronal injury comprises an ischemic and hemorrhagic stroke, spinal cord, brain, cranial nerve or peripheral nerve injuries.

13. The method of claim 9, wherein the neuronal injury comprises an ischemic stroke.

14. The method of claim 9, wherein the neuronal injury comprises a hemorrhagic stroke.

15. The method of claim 9, wherein the neuronal injury comprises a cranial nerve injury.

16. The method of claim 9, wherein the neuronal injury comprises a peripheral nerve injury.

* * * * *